(12) United States Patent
Tan

(10) Patent No.: US 9,849,456 B2
(45) Date of Patent: Dec. 26, 2017

(54) MICROFLUIDIC DEVICE

(71) Applicant: Clearbridge Mfluidics Pte. Ltd., Singapore (SG)

(72) Inventor: Swee Jin Tan, Singapore (SG)

(73) Assignee: Clearbridge Mfluidics Pte. Ltd., Singapore (SG)

( * ) Notice: Subject to any disclaimer, the term of this patent is extended or adjusted under 35 U.S.C. 154(b) by 0 days.

(21) Appl. No.: 15/037,747

(22) PCT Filed: Nov. 11, 2014

(86) PCT No.: PCT/SG2014/000528
§ 371 (c)(1),
(2) Date: May 19, 2016

(87) PCT Pub. No.: WO2015/084257
PCT Pub. Date: Jun. 11, 2015

(65) Prior Publication Data
US 2016/0296932 A1    Oct. 13, 2016

(30) Foreign Application Priority Data
Dec. 4, 2013 (SG) .............................. 201309079-0

(51) Int. Cl.
| *B01L 3/00* | (2006.01) |
| *G01N 15/14* | (2006.01) |
| *C12M 3/06* | (2006.01) |
| *G01N 33/49* | (2006.01) |
| *G01N 15/10* | (2006.01) |

(52) U.S. Cl.
CPC ....... *B01L 3/502761* (2013.01); *C12M 23/16* (2013.01); *G01N 15/1404* (2013.01);
(Continued)

(58) Field of Classification Search
CPC ............. B01L 3/502761; C12M 23/16; G01N 15/1404
See application file for complete search history.

(56) References Cited

U.S. PATENT DOCUMENTS 9,133,499 B2    9/2015    Di Carlo et al.
9,140,697 B2    9/2015    Tseng et al.
(Continued)

FOREIGN PATENT DOCUMENTS

CN    1860363 A    11/2006
CN    101548004 A    9/2009
(Continued)

OTHER PUBLICATIONS

Bo Huang, et al., Counting Low-Copy Number Proteins in a Single Cell, Science, 2007, vol. 315, p. 81-84.
(Continued)

*Primary Examiner* — Krishnan S Menon
*Assistant Examiner* — Dwan A Gerido
(74) *Attorney, Agent, or Firm* — Harness, Dickey & Pierce, P.L.C.

(57) ABSTRACT

Disclosed herein is a microfluidic device comprising, at least one sample inlet for receiving biological cells in a biological fluid sample; at least one sheath flow inlet for receiving a sheath fluid; at least one curvilinear channel configured to provide the biological fluid sample substantially in an outer flow and the sheath fluid in substantially an inner separated flow; a plurality of cell traps at the periphery of the curvilinear channel, each trap configured to admit a single cell having a targeted size range from the outer flow.

19 Claims, 6 Drawing Sheets

(52) U.S. Cl.
CPC .... *G01N 33/491* (2013.01); *B01L 2200/0636* (2013.01); *B01L 2200/0668* (2013.01); *B01L 2200/10* (2013.01); *B01L 2300/0627* (2013.01); *B01L 2300/0803* (2013.01); *B01L 2300/0864* (2013.01); *B01L 2300/12* (2013.01); *B01L 2400/0409* (2013.01); *B01L 2400/086* (2013.01); *G01N 15/1463* (2013.01); *G01N 15/1475* (2013.01); *G01N 2015/1006* (2013.01); *G01N 2015/149* (2013.01); *G01N 2015/1409* (2013.01); *G01N 2015/1415* (2013.01)

(56) References Cited

U.S. PATENT DOCUMENTS

| | | | |
|---|---|---|---|
| 2005/0207940 A1* | 9/2005 | Butler | B01L 3/502761 422/73 |
| 2010/0003666 A1* | 1/2010 | Lee | B01L 3/502761 435/5 |
| 2010/0066880 A1 | 3/2010 | Sato et al. | |
| 2010/0240041 A1 | 9/2010 | Matsunaga et al. | |
| 2012/0003711 A1 | 1/2012 | Tseng et al. | |
| 2012/0196314 A1* | 8/2012 | Nawaz | B01F 5/0647 435/29 |
| 2013/0171628 A1 | 7/2013 | Di Carlo et al. | |

FOREIGN PATENT DOCUMENTS

| | | |
|---|---|---|
| CN | 102405411 A | 4/2012 |
| CN | 103261436 A | 8/2013 |
| WO | 2005/022147 A | 3/2005 |
| WO | 2007/024701 A2 | 3/2007 |
| WO | WO-2007/145342 A1 | 12/2007 |
| WO | WO-2009/016842 A1 | 2/2009 |
| WO | WO-2010/108003 A2 | 9/2010 |
| WO | WO-2012/037030 A2 | 3/2012 |

OTHER PUBLICATIONS

Barry R. Lutz, et al., Hydrodynamic Tweezers: 1. Noncontact Trapping of Single Cells Using Steady Streaming Microeddies, Analytical Chemistry, 2006, vol. 78, No. 15, p. 5429-5435.

Joseph M. Martel, et al., Particle Focusing in Curved Microfluidic Channels, Scientific Reports, Nov. 26, 2013, vol. 3, Article No. 3340, p. 1-8.

Allison M. Schaap, et al., Continuous Size-Separation of Airborne Particles in a Microchannel for Aerosol Monitoring, IEEE Sensors Journal, Nov. 2011, vol. 11, No. 11, p. 2790-2797.

Qin, D., Xia, Y. & Whitesides, G.M. Soft lithography for micro—and nanoscale patterning. Nature Protocols, 5, 491-502 (2010).

Whitesides, G.M., Ostuni, E., Takayama, S., Jiang, X. & Ingber, D.E. Soft lithography in biology and biochemistry *Annual review of biomedical engineering* 3, 335-373 (2001).

International Search Report and Written Opinion of the ISA for PCT/SG2014/000528, ISA/JP, dated Feb. 17, 2015.

International Preliminary Report on Patentability and Written Opinion of the ISA (JPO) for PCT/SG2014/000528 dated Jun. 7, 2016.

Romanuik et al. "Microfluidic Trapping of Antibody-Secreting Cells", Journal of Medical and Biological Engineering, vol. 31(2), p. 121, Jan. 2011.

Noguchi et al., "Large Scale Microfluidic Systems for Sequential Trapping, Labeling and Content Extraction of Single Cells," Transducers, pp. 628-631, 2009.

Hou et al., "Isolation and Retrieval of Circulating Tumor Cells Using Centrifugal Forces," Scientific Reports, vol. 3, 2013.

Zhu et al., "Continuous-flow Particle and Cell Separations in a Serpentine Microchannel via Curvature-Induced Dielectrophoresis," Microfludics and Nanofluidics, vol. 11(6), pp. 743-752, 2011.

Nilsson et al., "Review of Cell and Particle Trapping in Microfluidic Systems," Analytica Chimica Acta, vol. 649(2), pp. 141-157, 2009.

Sajeesh et al., "Partcile Separation and Sorting in Microfluidic Devices: A Review", Microfluidics and Nanofluidics, 2014.

European Supplementary Search Report and Opinion regarding corresponding European Patent Application No. 14867110.0 dated Jun. 2, 2017.

Chinese First Office Action and Search Report in corresponding Chinese Patent Application No. 201480066231.0 dated May 9, 2017. Translation provided by Shanghai Patent and Trademark Law Office, LLC.

* cited by examiner

Fig. 4A(ii)

MICROFLUIDIC DEVICE

CROSS-REFERENCE TO RELATED APPLICATIONS

This application is a 371 U.S. National Stage of International Application No. PCT/SG2014/000528, filed Nov. 11, 2014, which claims the benefit of and priority to Singapore Patent Application No. 201309079-0, filed Dec. 4, 2013. The disclosure of each of the above applications is incorporated herein by reference in their respective entireties.

FIELD

The invention relates to a microfluidic device.

BACKGROUND

Every individual cell is unique and can differ by size, state, protein expression and can also exhibit distinct genomic profiles, even within the same tissue. These dissimilarities are important, especially in understanding rare diseases/cell events which are often masked out in population average measurements. For instance, detecting circulating tumour cells (CTC) in blood circulation is a potential non-invasive method for cancer prognosis. Beyond enumeration, which is correlated to tumour load, CTC characterization is expected to guide therapeutic selection for personalized care of patients. Single cell analyses can provide the critical piece of information that helps identify these changes. Conventional methods of extraction by pipetting and processing cells are tedious and error prone, especially when target cells are low in quantity and/or purity. Automated fluorescence cell sorters require millions of cells and introduce significant cell losses, which makes them unsuitable for this application.

Single cell analysis is gaining traction due to the potential benefits of addressing cellular heterogeneity. Important variations present in a small number of cells can be masked when analysis is performed on a cell population. Recovery and characterization of individual cells is therefore an essential part of many current studies in oncology and regenerative medicine. As medical practices gear towards personalized and targeted therapy; understanding the diversity and genetic makeup of cell populations will aid practitioners to better make clinical judgments. This will also speed up the drug design and screening processes, if we are able to identify the key mutations associated with the diseases. The ability to accurately select, manipulate and process single cells in a high throughput fashion is useful to obtain a sufficient sample size for understanding cellular heterogeneity.

Conventional bench top methods of single cell sorting and preparation include serial dilution and manual pipetting of cells under a microscope. To achieve single cell resolution using serial dilution results in large errors which are random and difficult to spot. Manual pipetting of cells is a fairly low throughput technique and operations are tedious, meaning that it will not be suitable for processing the hundreds of cells required to generate sufficient data points to characterize cellular subpopulation diversity patterns. Current semi-automated methods of isolation involving micropipette selection and using micro-manipulators or laser capture dissection are also low throughput processes, with the user having to navigate to the cells of interest individually to perform the isolation process.

Fluorescence activated cell sorter (FACS) has the ability to achieve single cell separation through optical interrogation. However, these systems require a sizeable amount of starting material and are less suited for rare cell events due to large cell losses. The FACS system is also a fairly expensive tool and is usually shared among several users, thereby risking contamination from sample to sample which might result in false positive outcomes in a subsequent genomic analysis. This limits the usefulness of the FACS system for rare specimens.

Other forms of cell sorters have been proposed, most notably using microsystems. These types of systems are favored due to low sample input requirements and allow a fairly reasonable throughput. These devices are also cheaper and allow for a single use to prevent cross contamination. Devices that make use of magnetic separation in a continuous flow had been shown to be highly efficient with enrichment as high as 5000 fold to discriminate against different cellular sub populations. The main limitation of such systems is that they do not allow for the recovery of single cells, which limits certain downstream analyses such as next generation sequencing (NGS), which is a useful tool to probe genetic variations on a large scale. Other sorting techniques which are considered gentle to the cells include separation through deterministic lateral displacement or by altering the laminar flow characteristics in micro flows. However, the velocities at which samples are traversing across the microchannels are too fast to make an accurate measurement of the fluorescence intensities without sophisticated equipment, which also makes the recovery of single cells difficult.

For systems that address sorting/recovery at the single cell level, these include micro patterning of substrates for single cell deposition, physical trapping using microfluidics, inkjet printing of cells and dieletrophoretic (DEP) forces that manipulate cells at its active probing region. For instance, it will be difficult to use micropatterning for specific cell recovery to perform DNA extraction for molecular analysis without affecting adjacent adhered cells. Sophisticated controls for systems using dielectrophoresis (DEP) forces and inkjet printing of cells are additional costs which are significant. For example, a major limitation of the Fluidigm™ single cell sample preparation system, which uses passive physical trapping, requires target cells of higher than 1.1% frequency because there are only 96 wells within the system. If the frequency of the desired cells is lower than 1.1%, then there is a good probability that none of the target cells will be extracted out of the run. Even so, much of the sample within the system is wasted as most are not the target cells, unless the input is relatively pure. Therefore, there remains a need for a system that can enable the speedy recovery of cells, but which is also sufficiently flexible to enable archival of the cells or enables the use of said cells in various downstream applications.

SUMMARY

In general terms the invention proposes a microfluidic device that captures individual cells from a high flow channel, and individually ejects them for single cell analysis. This may allow high speed processing and/or optical/fluorescence interrogation. Recirculation may maximize cell recovery which may specifically target rare cell events and low cell input samples where the quantity of the sample is a limiting factor. The device may provide a comprehensive sample preparation tool capable of delivering multitudes of single cells and provides basic cellular attributes such as morphological information and protein expression levels through immunocytochemistry.

In a first aspect of the invention, there is disclosed microfluidic device comprising:

- at least one sample inlet for receiving biological cells in a biological fluid sample;
- at least one sheath flow inlet for receiving a sheath fluid;
- at least one curvilinear channel configured to provide the biological fluid sample substantially in an outer flow and the sheath fluid in substantially an inner separated flow; and
- a plurality of cell traps at the periphery of the curvilinear channel, each trap configured to admit a single cell having a targeted size range from the outer flow.

The plurality of cell traps at the periphery are configured to be in fluid contact with the outer flow.

The device may further comprise an ejector configured to eject each single cell having the targeted size range from each trap during an ejection mode.

The cell traps may include a first port proximate the outer flow and configured to admit the single cell having the targeted size range and a second port distal the outer flow. The second port may be configured to provide a lower pressure relative to the outer flow during a trapping mode. For example, the lower pressure is ambient atmospheric pressure.

The second port may be further configured to provide a high pressure during the ejection mode. For example, the high pressure may be provided with a flow of sheath fluid.

The second port may be selected from the group consisting of a weir, a constricted channel, an optically switched gate, and a dielectrically switched gate. For example, when the second port is a weir, the weir has a narrowest dimension less than 5 μm, such as a narrowest dimension of from 1 to 3 μm.

The first port may be from 10 μm to 30 μm, 15 μm to 25 μm, 16 to 21 μm or 17 to 20 μm in width.

The device may further comprise an optical system. For example, the optical system may be suitable for selecting a targeted cell type, optionally wherein the optical system is configured for use in brightfield or fluorescence imaging. The targeted cell type may be a circulating tumour cell.

The at least one sample inlet may be configured to control the volume and flow rate of the biological fluid sample and/or the at least one sheath inlet is configured to control the volume and flow rate of the sheath fluid. For example, the respective volume and flow rates of the biological fluid sample and sheath fluid are configured to achieve an outer flow width of 15-25 μm.

The channel may be flushed between the trapping mode and the ejection mode.

The device may be moulded from PDMS or a hard plastic bonded onto a glass slide.

The device may further comprise an optical detector configured to determine the presence of a cell within each trap and/or the type or identity of the cell within each trap.

The device may further comprise a recycling port configured to recirculate the fluid sample through the channel.

The device may further comprise an outlet configured to provide each ejected single target cell to a predetermined location.

In a second aspect of the invention, the fluid delivery system comprises:

- an inlet configure to receive biological fluid;
- a microfluidic device according to claim 23, wherein the at least one sample inlet of the microfluidic device is coupled to the biological fluid sample inlet of the system and the at least one sheath flow inlet of the microfluidic device is coupled to the sheath fluid inlet of the system,
- a diagnostic or analysis module configured to process each ejected single cell having the targeted size range from the output of the microfluidic device for diagnosis or analysis, and
- a controller configured to send control signals during the trapping mode to the at least one inlet until all of the traps are full, and to send control signals to the ejector during ejection mode to sequentially eject the cell having the targeted size range from each trap.

The fluid delivery system may further comprise an output array configured to be translatable relative to the output of the microfluidic device, wherein each ejected single cell having the targeted size range from the output is provided to a separation location within the array.

The diagnostic or analysis module may be configured to extract each ejected single cell having the targeted size range from the output array for single cell analysis.

BRIEF DESCRIPTION OF THE FIGURES

The invention will now be described in further detail below, with the aid of the following figures.

DETAILED DESCRIPTION

Figure 1A:
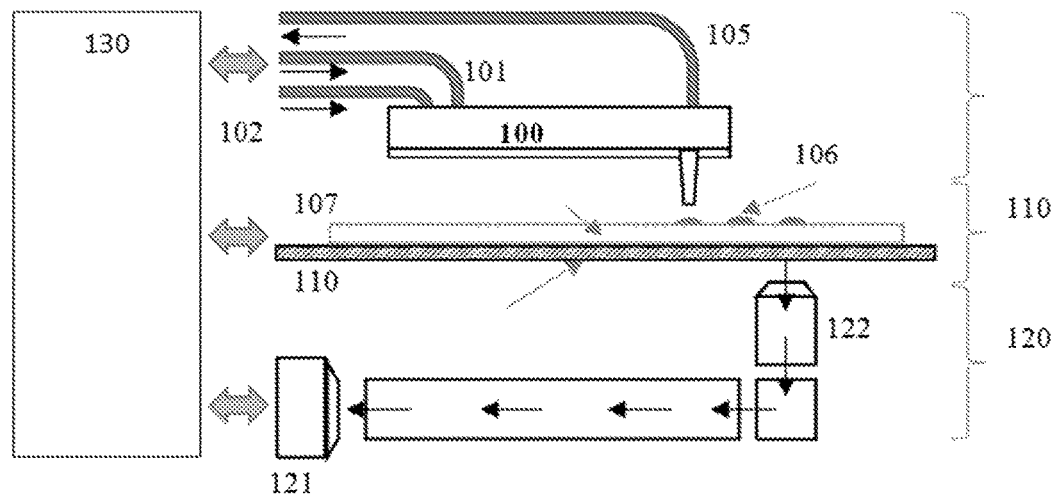
FIG. 1A is a schematic diagram of a system architecture for cell isolation and recovery.

A system for sorting and isolating single cells is illustrated in FIG. 1. A microfluidic device (100) that has the capability for low cell input and controlled cell dispensing onto a substrate (106), this can optionally be an automated stage (110) that allows precise positioning of the cell recovery, and an optical setup (120) for imaging and feedback (e.g. including a camera (121) and an objective (122)). The device may further comprise a computer interface (130), a sample input (101), a sheath flow input (102), a sample recycling port (105) and a sample recovery tray (107) placed on the an x-y stage (111).

The system is able to sort and provide single cells in the order of thousands of cells onto a recovery substrate, which can then be immediately used in subsequent downstream analyses. The recovery substrate is an exchangeable platform capable of holding different types of media, such as a common glass slide typically used for cellular imaging or well plates (different sizes) used in PCR and cell culture. For instance, if the user is interested in identifying a subpopulation of cells within its input sample pool through immunocytochemistry or fluorescence in-situ hybridization, the cells can be immobilized onto poly-L-lysine coated slides during cell recovery and subsequently incubated with antibodies of interest for the study in question. A suitable substrate may be chosen depending on what is to be done to the cells (e.g. they type of analysis that the cells are to be subjected to). The imaging setup on the system will also be able to provide fluorescence scans to discriminate against the different cellular sub-types present. Furthermore, as the positioning of each cell is predetermined by the system, the substrate can be easily archived for future analysis if needed.

A potential downstream application that will greatly benefit from the single cell sample preparation system is next generation sequencing (NGS). NGS is a growing and important application that has brought about a paradigm shift in the biomedical sciences, with a profound impact on the understanding of genetic variations, and improved clinical assessments. By choosing a suitable recovery substrate, such as a 96/384 well PCR plate, this will be directly compatible with existing platforms to perform the cell lyses and subsequent sequencing library preparations. The possibilities for prospective downstream applications benefiting from this sample preparation system are limitless and it will enhance the productivity of current detection methods by providing higher throughput.

Figure 2:
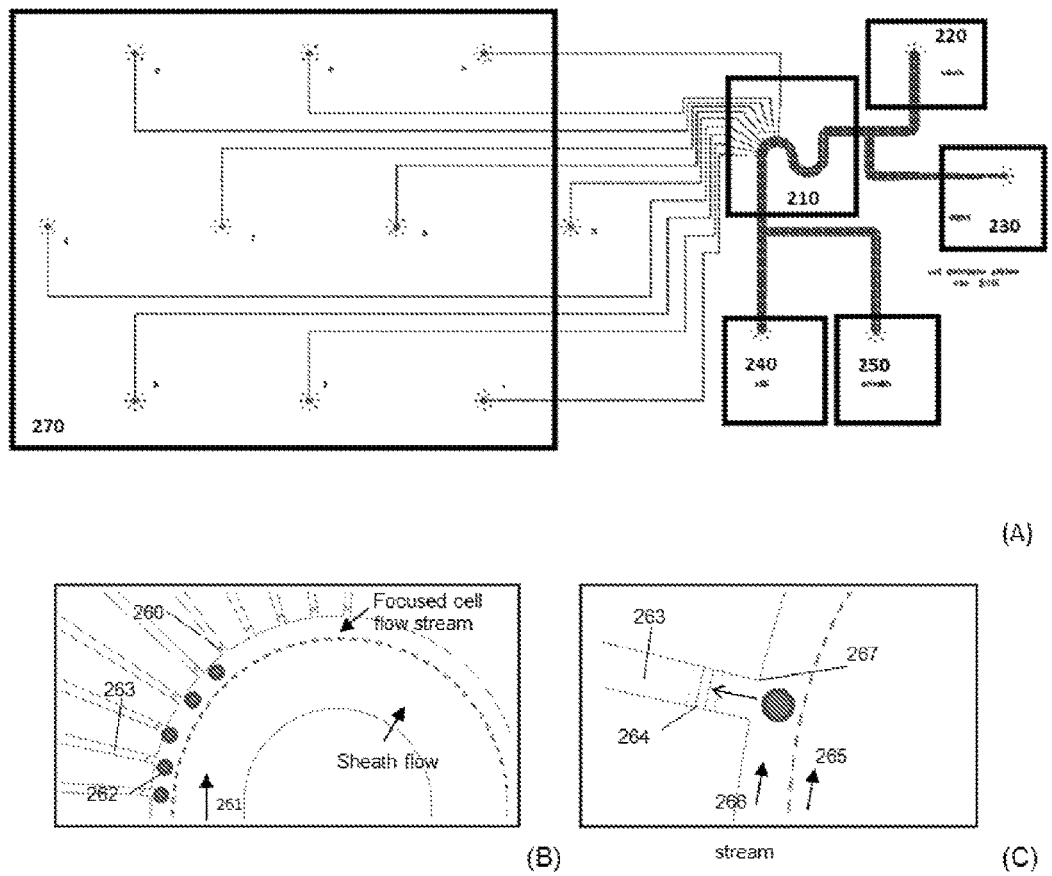
FIG. 2 (A) is a Computer aided design (CAD) layout of the microfluidic device, (B) is a schematic of the cell capture region showing the position of the flow streams and the cell chambers and (C) is a schematic of forces acting on the cell as it approaches the cell chamber.

The design of a microfluidic device 100 is depicted in FIGS. 2A and 2B. This device may contain a single cell isolation portion (210), a recycling port (220), a recovery port or outlet (230), a cell flow inlet (240) and a sheath flow inlet (250). The single cell isolation portion (210) includes a hydrodynamic focusing region 261 and a series of cell holding chambers or cell traps 260, spaced around the periphery of the hydrodynamic focusing region 261. The device also includes a cell ejection control portion 270.

Such devices may be moulded from PDMS via soft lithography, hot embossing methods or injection moulding.

In the depicted system, as shown in FIGS. 2A and 2B, the hydrodynamic focusing region (261) is annular, extending over a 180° curvilinear arc. There are 10 holding chambers (260) located around outer edge. As will be appreciated, the number of cell holding chambers may be greater or less than 10, for example there may be 2 to 200 cell holding chambers (e.g. 4 to 100 cell holding chambers, such as 5 to 50 cell holding chambers). The cell holding chamber (260) has a first port (267) that opens into the hydrodynamic focusing region (261) and a second distal port (264).

It will be appreciated that there is no limit or specific design consideration on the spacing or the curvature of the channel.

In order to achieve minimal losses and high speed isolation of cells, input cells (262) are focused to the side of the channel wall (FIG. 2B) by a sheath flow and pushed into the first port 267 as is passes. A combinatory effect of centrifugal forces and a slight negative pressure differential (FIG. 2C) on the cell favours its entry into the cell holding chamber. The negative pressure in the cell holding chamber can be obtained by venting the cell holding chambers to the atmosphere via a cell ejection port (263), from the second port (264), while a positive pressure is applied to drive the bulk fluid through the semi-circular bend. The cell is impeded from the cell ejection port (263) by the weir structure (264) of height 2 µm (e.g. 1.8 to 2.2 µm) in the depicted embodiment. Alternatively, the weir in the cell holding chamber may be replaced by an optically switched gate or a dielectrically switched gate. Once the cell chamber is occupied, the resistance to further cell entry becomes high and the next incoming cell is likely to roll across to the next impending cell holding chamber. With this approach, the depicted device is able to hold up to 10 cells at a time and this can be verified by the imaging system. This is shown in the image of FIG. 5B, where each chamber can be seen to be occupied by a single cell.

The device may be designed to capture CTCs, but may equally be designed for the isolation of any cell types, optionally excluding red blood cells and platelets. For example the dimension of the weir (264) and the chamber (260) depend on the target cell size. For a CTC of approximately 15 µm diameter, the chamber (260) should be between 16-21 µm wide (e.g. 17-20 µm), and the weir gap should be 0.5 µm to about 5 µm (e.g. 1 µm to 3 µm, such as 1.5 µm to 2.5 µm, e.g. 2 µm).

In order to ensure that the cells are captured by the cell holding chambers, the flow of the sheath flow (265) and the cell flow (266) are optimized such that the cell flow stream has to be of similar width to the dimensions of the cells that have been targeted. This enables the cells in the cell flow stream to be as close to the chamber as possible. For example, when the selected cells have a size of 15 µm, the targeted width of the cell flow is in the range of 15-25 µm. Optionally, a sheath flow of higher viscosity can be used to minimize waste volume (e.g. the viscosity of the liquid used as the sheath flow may be 2 to 10 times, such as 2 to 4 times, such as 3 times that of the liquid used as the cell flow vehicle). Any suitable syringe pump may be used for the cell flow and sheath flow lines and the system may be controlled by a computer running control software.

Figure 1B:
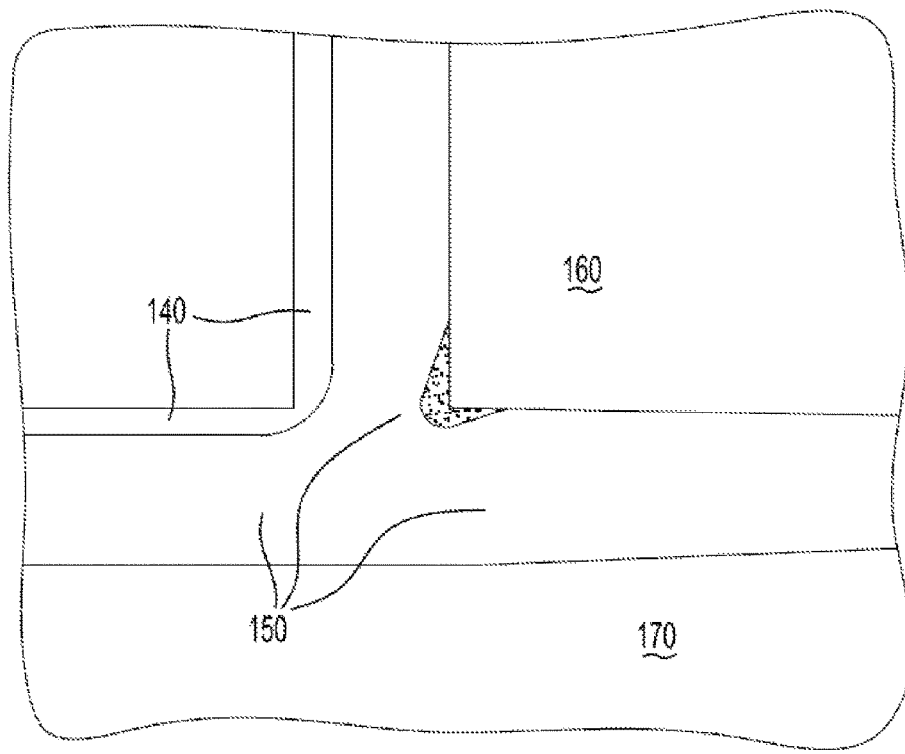
FIG. 1B is an image depicting a view of the exit channel of a device, wherein a coloured dye has been used to differentiate between the biological sample fluid flow and the sheath fluid flow.

The conditions used above essentially ensure that the two flows will not mix due to the laminar characteristics of each flow. Diffusion between the separate flows is also minimized as the length of the channel is relatively short. FIG. 1B, depicts a 90° bend of the exit channel (160, 170), but this is similar to the bends found between the chambers in the peripheral wall of the channel and the outer flow. FIG. 1B shows that these flows do not mix but that one flow (the outer flow; 140) is compressed against the peripheral wall by the other flow (the inner flow; 150).

While the vast majority of cells will remain in the biological sample fluid, or outer, flow (140), there may be some exceptions. These exceptions are larger cells whose centre of mass exceeds the focus stream dimensions of the biological sample fluid flow and will end up following the stream line of the sheath, or inner, flow (150).

The sheath flow liquid may comprise any suitable cell compatible buffer. For example, the sheath flow liquid may contain a varying concentration of glycerol mixed with water/phosphate buffered saline (PBS). Other suitable sheath flows may include polyethylene glycol or dextran in varying concentrations mixed with water/PBS. It will be appreciated that the sheath flow may contain a combination of any of glycerol, polyethylene glycol and dextran at varying concentrations mixed with water/PBS.

For example, during the trapping phase the flow rate may be between 100-400 µL/min with a sheath to cell flow fluid viscosity ratio of approximately 3:1. The volumetric ratio of cell to sheath flow rate (in mL per second) may be from about 1:1 to about 1:5 and the concentration of the sample may be greater than or equal to 100 cells per mL (e.g. from about 1,000 cells per mL to about 2,000,000 cells per mL, for example from about 2,000 cells per mL to about 1,000,000 cells per mL). Using these parameters, it is expected that the filling of all cell holding chambers will take from almost instantaneous filling to 30 minutes (e.g. 0.01 seconds to 10 minutes, such as 0.1 seconds to 120 seconds). It will be appreciated that the time to fill all of the chambers will vary according to the concentration of the cells in the fluid sample.

In respect of CTCs, it is estimated that the concentration of such cells in a pre-enriched blood sample is typically about 1 cell in one billion blood cells. However, for an enriched sample the concentrations of CTCs may be about 1 cell in 1000-10,000 blood cells. Once the cell flow and the sheath flow have passed the hydrodynamic focusing region and the cell holding chambers, the flows are directed to a recycling port. Optionally, the recycling port is bifurcated to enable a better separation between the sheath flow and the cell flow, particularly when the sheath flow has a higher viscosity than the cell flow.

After all of the chambers are full, the hydrodynamic focusing region may be flushed (e.g. with any suitable cell buffer or nuclease-free water).

Then the ejection phase begins. Each cell is individually released onto the recovery substrate by applying a positive pressure to the respective cell chamber (cell ejection control in FIG. 2A). The recovery substrate may be any suitable substrate, for example a moveable recovery tray or a 96/384 well PCR plate. The positive pressure applied to the cell may be in the form of a suitable liquid (e.g. any suitable cell buffer or nuclease-free water) that enters the cell holding chamber through the cell ejection port (e.g. by application of pressure from any suitable syringe pump), thereby ejecting the cell into the semi-circular bend and directing the cell to a recovery port. During the trapping phase, the recovery port 230 is closed The selection of the recovery port is controlled through calibration of the device so that the recovery port is selected when the ejection fluid is applied through the ejection port for the correct period of time and at the correct pressure (e.g. the application of 1 µL in 3 seconds in the pressure range of 1-5 Psi). Optionally, before the cells are, released from their individual cell holding chambers, the hydrodynamic focusing region (i.e. the semi-circular bend) may be flushed with any suitable liquid.

It will be appreciated that the user has the option to dispense each cell individually or any other possible combination, up to and including all of the cells trapped in the cell holding chambers. It will be further appreciated that the ejection of the cell can be varied according to the desires of the operator and may be changed for each ejection run. This flexible dispensation system allows for titration experiments to be conducted in certain studies.

Another important feature of the device is the ability to recycle (lost samples) that failed to enter the cell chambers on the first (or subsequent) passes. As the system is targeted at applications where the quantity of the desired cellular samples is limiting or rare, it is vital to ensure maximum recovery of the input cellular materials. This is accomplished by routing the focused cell stream from the recycling port (220) back into the cell flow inlet (240) where the cells will get a further chance of being accepted into the cell holding chambers. The cycle of cell isolation repeats until the cellular sample input is depleted. For example, depletion of a recycled sample may be determined in an automated version of the device by setting the device to stop recycling the sample when no cells are captured over a period of 5 minutes.

If optics are used to review whether all of the chambers are filled (prior to dispensing), then those optics can also be used to select the cells of interest. For example optical systems may make use of brightfield or fluorescence imaging. This allows the operator to get rid of noise or unintended cells. For example, in the depicted device, after all of the ten chambers are filled, if chamber 5 is the only chamber that has a cell of interest (the target cell) then that cell can be dispensed onto a plate/slide while the other nine cells can be dispensed simultaneously to the waste. This waste may be the recycling port or a separate waste port. Such a sample can readily be fed into any single cell analysis platform. This eliminates the need to move the slide/plate to a cell-picking station to select the cells of interest from a massively parallel plate of single cells.

The depicted system can be used as an aid in sample preparation at large sequencing laboratories, or at central pathology laboratories where frequent immuno-cytochemistry, fluorescence in situ hybridization (FISH) and other molecular methods are carried out. The system can also serve cell/molecular biology laboratories, providing them with a full analysis on single cells with its integrated imaging capabilities to address cellular diversity. The depicted system has already been used to prove the concept of cell isolation and recovery with the microfluidic design, as described below.

The system is a significant advance over current research endeavours on circulating tumour cell (CTC) isolation and detection that further bridges the gap between research establishments and clinical settings. With the depicted system's ability to prepare samples for downstream analysis, it enables a more sensitive measure to detect mutations and variations which are currently masked by the presence of significant amounts of white blood cells. For instance, the gold standard of mutational analysis using conventional PCR and Sanger sequencing has a limit of detection at 1% which is usually not attainable with samples with low CTC counts. The depicted system can ensure that there is sufficient sample purity before performing downstream analysis.

Experimental Section

Manufacture of Device

Proof of concept experiments have been pursued with devices fabricated using PDMS via soft lithography (e.g. see the methods described in Qin, D., Xia, Y. & Whitesides, G. M. Soft lithography for micro- and nanoscale patterning. *Nature protocols* 5, 491-502 (2010) and in Whitesides, G. M., Ostuni, E., Takayama, S., Jiang, X. & Ingber, D. E. Soft lithography in biology and biochemistry *Annual review of biomedical engineering* 3, 335-373 (2001) incorporated herein by reference).

Proof of Concept

Figure 3A:
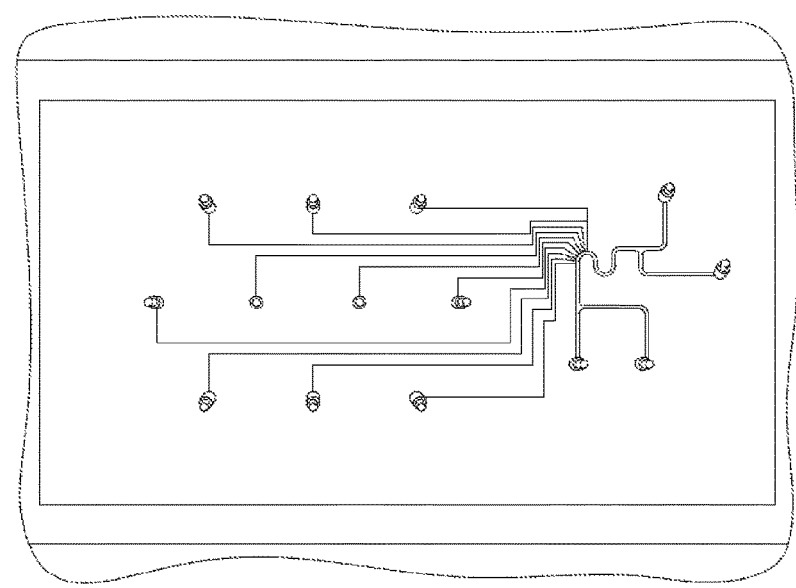
FIG. 3 (A) is an image of a prototype device fabricated using PDMS bonded onto a glass slide, and (B) is an image of the device in operation using colour dye visualization.

FIG. 3A shows a prototype device used to characterize the efficacy of the single cell capture and recovery concept, which uses 15 µm polystyrene beads as ideal test samples. The device is compatible with most existing inverted or upright microscopes, so minimizes any additional cost, and permits real time visualization of the isolation process. However, an integrated microscope may be incorporated into the device. As depicted, the device is connected and tested using syringe pumps with connecting tubes arranged as shown in FIG. 3B.

This system results in high isolation rates, when used with an optimized hydrodynamic focused cell flow and also illustrates the potential of recycling lost cells back into the system so that the total cell recovery rate can be enhanced. This system also allows the positive recovery of single beads by applying a positive pressure to the desired cell chamber and this visually verification of the retrieval was obtained by optical imaging.

Optimised Sheath Flow

Figure 3B:
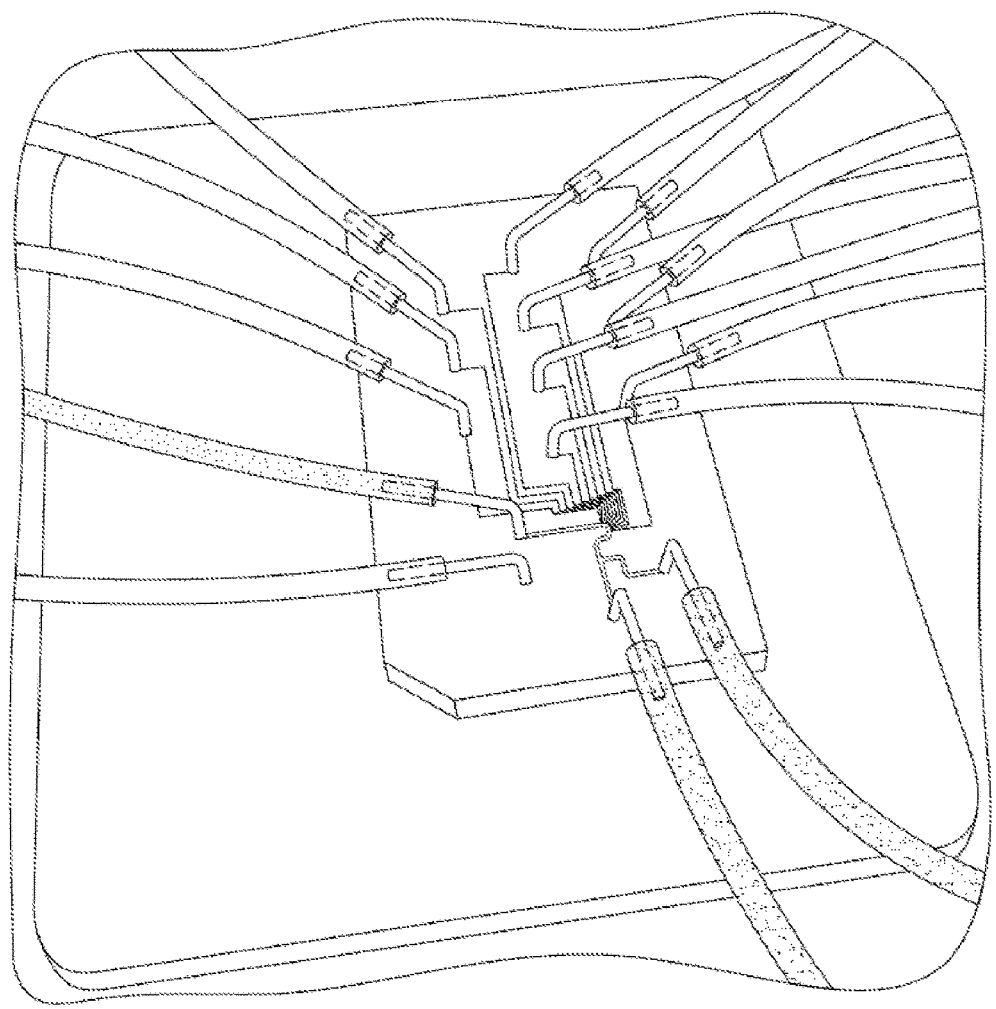

Flow control within the device of FIGS. 3A and 3B is important, as this directly affects the isolation efficiency of the beads into the cell chamber. The criteria for an optimized flow is that the cell flow stream has to be of similar width to the dimensions of the cells. In this case, the targeted width is in the range of 15-25 μm to match the size of the beads that are being used as "cells". This enables the "cells" in the cell flow stream to be as close to the chamber as possible. Furthermore, in order to minimize the waste volume, a sheath flow of higher viscosity was selected, thereby changing the hydrodynamic spreading during the sample processing step. This allowed easy maintenance with minimal waste generated and eased selection of pumps as the final fluid lines ratio will not be too divergent.

In the current example, an NI Labview (National Instruments, USA) interface for the control of two syringe pumps that feed both the cell and sheath flow lines is used. The software provides an active regulation of the flow rates of each flow line without having to manually change the parameters on the pump each time. It also helped to synchronize the start of the pumps to minimize transient responses of the system. This software currently controls 2 syringe pumps. These syringe pumps may be replaced with solenoid valves for pressure control. A total of up to 24 valves/syringe pumps may be implemented using such software.

Flow rates between 100-500 μL/min with a sheath to cell flow fluid viscosity ratio of approximately 3:1 were investigated. This ratio of fluid viscosities was selected after numerous tests. The cell flow was simulated using deionised (DI) water while the sheath flow used a food colour dye that was significantly more viscous. The coloured dye is diluted with DI water until it is approximately three times more viscous than DI water alone. The viscosities were measured using a rheometer.

Figure 4A:
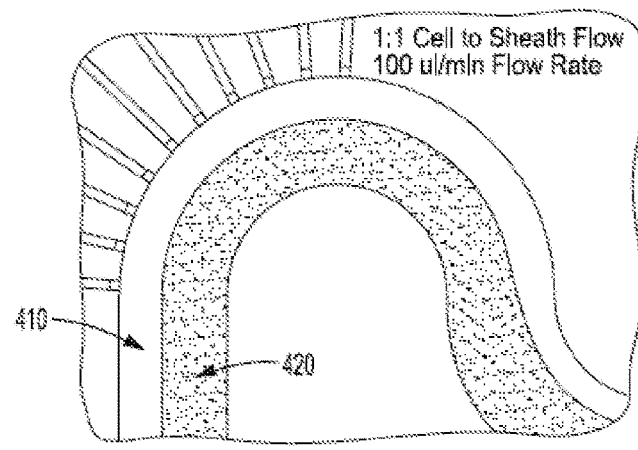
FIG. 4 (A) (i) and (ii) are images of the cell flow line, and (B) is a graph of the correlation between flow ratio and width of cell flow line.

FIG. 4A shows a typical characterization experiment performed at 100 μL/min and using either a 1:1 (FIG. 4A(i)) or a 1:5 (FIG. 4A(ii)) cell (410) to sheath flow (420) rate ratio. As can be seen in FIG. 4A, simply changing the rate of flow enabled the focused cell flow width to be controlled within the desired dimensions.

Figure 4B:
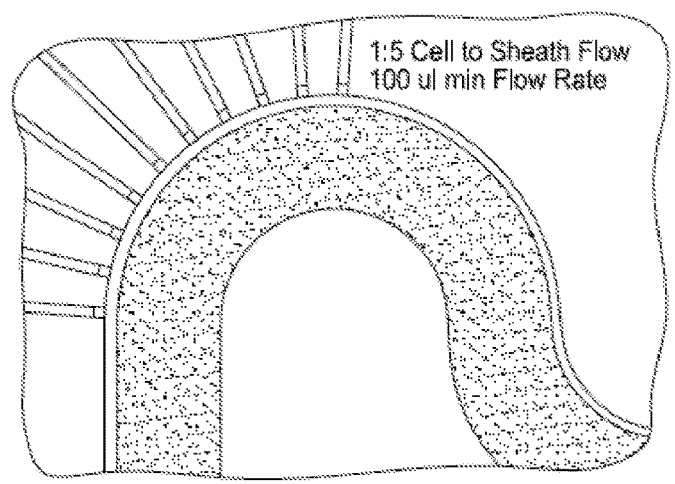
Figure 4B:
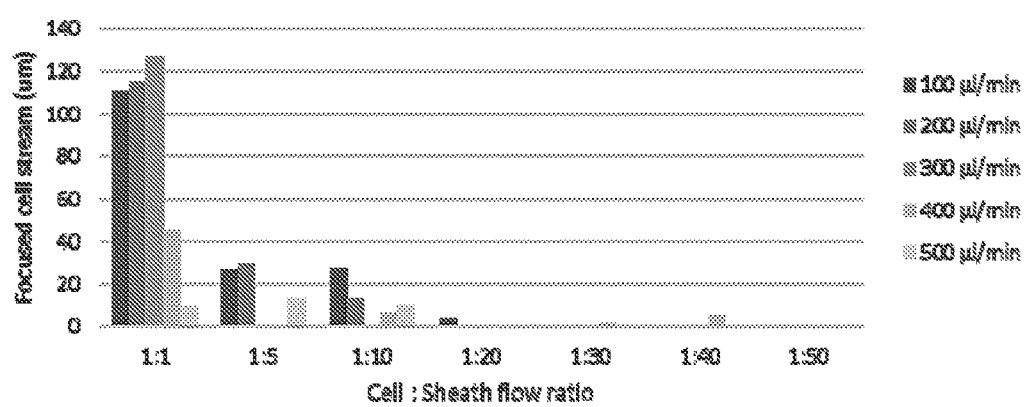

From FIG. 4B, it is observed that above a flow rate of 400 μL/min, the sheath flow totally dominates the flow in the channel resulting in an uneven pulsating cell flow stream. Therefore, the maximum processing limit of the system is designated as being 400 μL/min. Given this, for a typical input sample of 1000-2000 μL, the first pass processing time is in the range of 5 to 10 minutes, assuming a 1:1 cell to sheath flow ratio. In the process of running such samples, a 1-2 mL sheath flow waste is generated as compared to a 10 to 20 mL if we were to use fluids of the same viscosity in the cell and sheath flows.

Isolation Efficiency and Sample Recovery

Using 15 μm polystyrene beads to simulate cells, the effects of particle concentration introduced into the system at various inlet flow rates was investigated. This allowed the processing time required for samples of varying initial conditions to be gauged and to determine if pre-preparation of the sample (dilution or sample concentration) is required prior to loading onto the device. An optimal input concentration range will allow regular passage of single cells within tolerable time intervals. Conversely, if the concentration is too high, this may result in large losses of input cells because there is a small lag time before the cell flow can be stopped when all the cell chambers are occupied. However, a low concentration will result in a long waiting time before the chambers are completely filled and this will lengthen the processing time.

Figure 7:
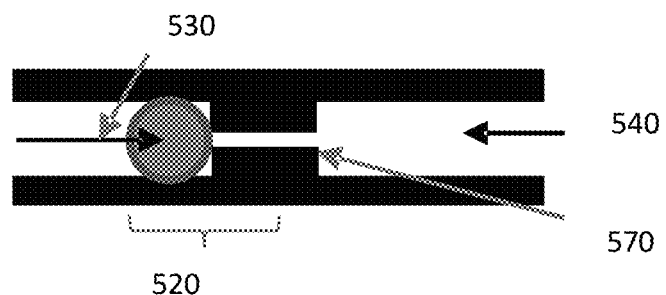
FIG. 7 is a schematic diagram showing an alternative mechanism for cell isolation and recovery.

FIG. 5A illustrates the mechanism for cell isolation and recovery. The weir structure (510) in each cell chamber (520) allows a cell to be held in the recessed chamber until it is ready to be retrieved. This is achieved by the combinatory effect of negative pressure and centrifugal forces around the bend (530). As the chamber is located alongside the main flow, the isolated cell will not be adversely affected by the flow in the main channel. This enables the main channel to be flushed before retrieval of the trapped cells. The release mechanism is straightforward and words by applying a positive pressure (540) to the opposing end of the weir step. FIG. 7 illustrates an alternative arrangement, wherein the weir structure (510) in FIG. 5A is replaced by a constricted channel (570) in the cell holding chamber. In the depicted examples, the constricted channel and the weir structure provide a gap of 2 μm, though any size disclosed herein may be used.

Figure 5:
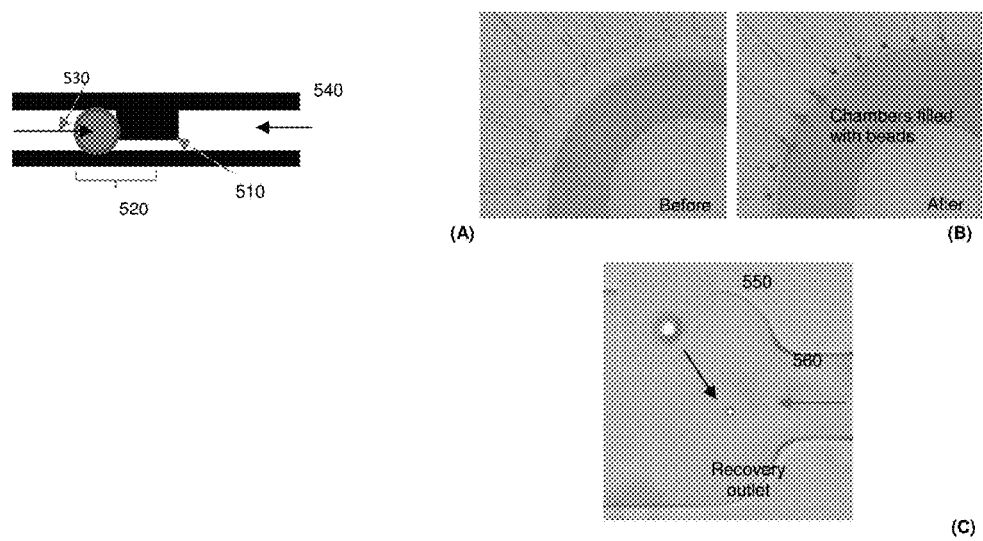
FIG. 5 (A) is a schematic diagram of the mechanism for cell isolation and recovery, (B) is an image of cell isolation within the cell chamber taken using an optical microscope, and (C) is an image of cell recovery and verification via optical imaging.
Figure 6:
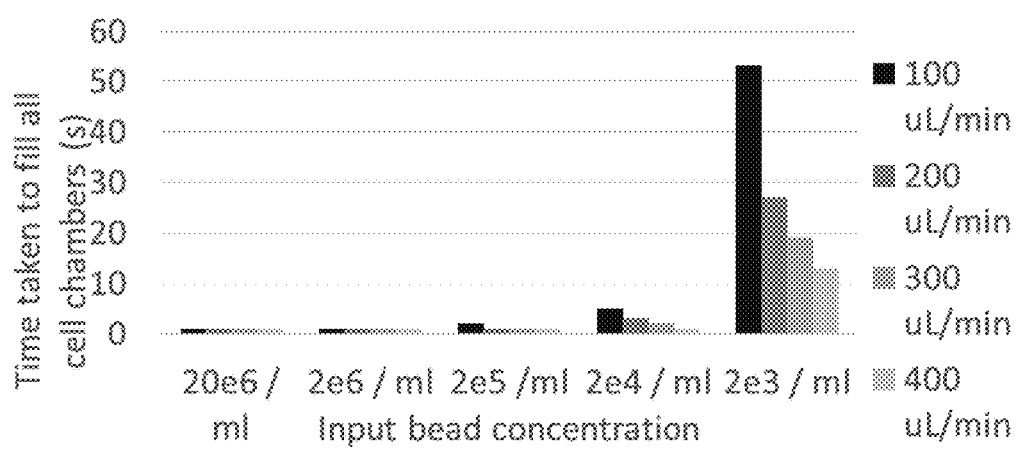
FIG. 6 is an image of efficiency of cell capture within all 10 chambers taken using an optical microscope.

In the currently depicted device, flow conditions of 1:5 for cell to sheath flow rates were used with varied total flow rates of from 100 to 400 μL/min. The time taken to occupy all 10 of the cell chambers were noted and averaged based upon five independent runs. The faster it takes to fill the chambers will enhance the throughput of the system. FIG. 5B shows successful bead isolation in the chambers in a typical test run. In the current example, the input bead concentration was varied from 2000 beads per mL of DI water to 20 million beads per mL. FIG. 6 summarizes the different operating conditions investigated. At 0.2 million beads per mL and beyond, the bead isolation is almost instantaneous at all different flow rates tested. At the lower concentration of 2000 beads per mL, the time taken to fill all 10 cell traps was 53 seconds when the flow rate was set at 100 μL/min. Increasing the sample flow rate reduced the capture time to 13 seconds. That is, changing the flow rate to 400 μL/min resulted in a 75% improvement in the time taken to fill the cell traps. Thus the system is well positioned to handle input samples with concentration 0.2 million cells per mL and above and it is possible adjust the system to run at higher flow rates for lower concentration samples to maximize throughput.

FIG. 5C shows the successful recovery of a bead (550) at the recovery outlet of the device (560). To enable visualization of the ejection process from the cell chamber, a large diameter biopsy punch (5 mm) was used to create a collection well at the recovery fluidic port. The ejected, bead was removed by manual pipetting and the next bead chamber was then activated to dislodge and recover the next bead. This was done until all of the beads had been recovered sequentially. In 100 different trials, the system was successful removing and recovering all 100 beads individually.

Figure 8:
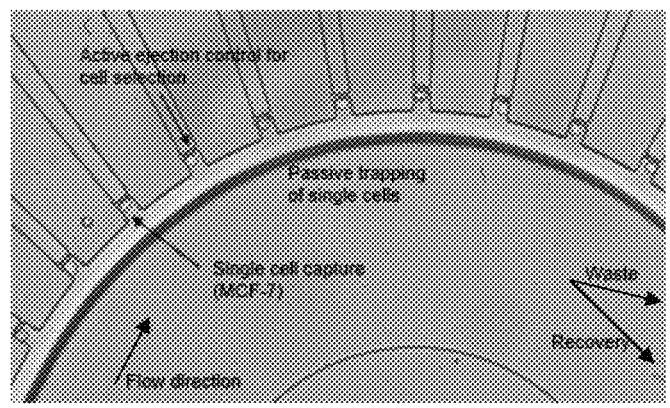
FIG. 8 is an image of cell isolation within the cell chamber taken using an optical microscope.

As mentioned in this experimental section, polystyrene beads were used to simulate cells. FIGS. 5A to 5C illustrate the mechanism, isolation and recovery of the beads under specified conditions. FIG. 8 shows the successful isolation of single MCF-7 cancer cells using the device according to the present invention. The same conditions as those described in relation to FIG. 5 were used. As can be seen from FIG. 8, the efficiency of single cell capture is 100% by activating the ejection control for each cell holder in the semi-circular serpentine.

The invention claimed is:

1. A microfluidic device comprising:
   at least one sample inlet for receiving biological cells in a biological fluid sample;
   at least one sheath flow inlet for receiving a sheath fluid;
   at least one curvilinear channel defining an arc region configured to provide the biological fluid sample substantially in a stable outer layer flow and the sheath fluid in substantially a stable inner layer separated flow; and
   a plurality of cell traps at the periphery of the arc region of the curvilinear channel, each trap configured to admit a single cell having a targeted size range from the outer layer flow.

2. The device of claim 1, further comprising an ejector configured to eject each single cell having the targeted size range from each trap during an ejection mode.

3. The device of claim 2, wherein the cell traps include a first port proximate the outer flow and configured to admit the single cell having the targeted size range and a second port distal the outer layer flow.

4. The device of claim 3, wherein the second port is configured to provide a lower pressure relative to the outer layer flow during a trapping mode.

5. The device of claim 3, wherein the second port is further configured to provide a high pressure during the ejection mode.

6. The device of claim 3, wherein the second port is selected from the group consisting of a weir, a constricted channel, an optically switched gate, and a dielectrically switched gate.

7. The device of claim 6, wherein the weir has a narrowest dimension less than 5 μm.

8. The device of claim 2, wherein the at least one sample inlet is configured to control the volume and/or flow rate of the biological fluid sample.

9. The device of claim 8, further wherein the at least one sheath inlet is configured to control the volume and/or flow rate of the sheath fluid.

10. The device of claim 9, wherein a viscosity of the sheath fluid is between 2 to 10 times, between 2 to 4 times, or approximately 3 times that of the biological fluid sample.

11. The device of claim 10, wherein the viscosity, respective volume and/or flow rates are configured to achieve an outer layer flow width of 15-25 μm.

12. The device of claim 2, which is configured to flush the channel between the trapping mode and the ejection mode.

13. The device of claim 2, wherein the device is moulded from PDMS or a hard plastic bonded onto a glass slide.

14. The device of claim 2, further comprising an optical detector configured to determine the presence of a cell within each trap and/or the type or identity of the cell within each trap.

15. The device of claim 14, wherein the optical detector is suitable for selecting a targeted cell type.

16. The device of claim 15, wherein the targeted cell type is a circulating tumour cell and/or the targeted size range is 10 μm to 30 μm.

17. The device of claim 2, further comprising a recycling port configured to recirculate the fluid sample through the channel.

18. The device of claim 2, further comprising an outlet configured to provide each ejected single cell to a predetermined location.

19. The device of claim 1, wherein the arc region extends over at least 180°.

* * * * *